United States Patent
Kranner et al.

(10) Patent No.: US 9,844,450 B2
(45) Date of Patent: Dec. 19, 2017

(54) FOOT PROSTHESIS

(71) Applicant: Ossur Iceland ehf, Reykjavik (IS)

(72) Inventors: Werner Kranner, Bad Aibling (DE);
May Eppensteiner, Irschenberg (DE);
Volker Nissels, Bayreuth (DE); Jan Hertwig, Rosenheim (DE)

(73) Assignee: OSSUR ICELAND EHF, Reykjavik (IS)

( * ) Notice: Subject to any disclaimer, the term of this patent is extended or adjusted under 35 U.S.C. 154(b) by 12 days.

(21) Appl. No.: 14/945,923

(22) Filed: Nov. 19, 2015

(65) Prior Publication Data

US 2016/0143750 A1    May 26, 2016

(30) Foreign Application Priority Data

Nov. 25, 2014   (DE) .......................... 10 2014 117 210

(51) Int. Cl.
*A61F 2/50*  (2006.01)
*A61F 2/66*  (2006.01)

(52) U.S. Cl.
CPC .......... *A61F 2/66* (2013.01); *A61F 2002/503* (2013.01); *A61F 2002/5007* (2013.01); *A61F 2002/5033* (2013.01); *A61F 2002/6614* (2013.01); *A61F 2002/6657* (2013.01)

(58) Field of Classification Search
CPC ....................................................... A61F 2/66
See application file for complete search history.

(56) References Cited

U.S. PATENT DOCUMENTS

| 4,959,073 | A | * | 9/1990 | Merlette | ................... A61F 2/60 623/27 |
| 6,572,659 | B1 | * | 6/2003 | Ryan | ......................... A61F 2/66 623/52 |
| 8,540,781 | B2 | | 9/2013 | Nissels et al. | |
| 8,945,238 | B2 | | 2/2015 | Mosler et al. | |
| 2010/0042228 | A1 | | 2/2010 | Doddroe et al. | |
| 2012/0046760 | A1 | | 2/2012 | Nissels et al. | |
| 2013/0261767 | A1 | | 10/2013 | Kranner et al. | |

(Continued)

FOREIGN PATENT DOCUMENTS

| DE | 10393458 T5 | 10/2005 |
| DE | 102006004132 A1 | 8/2007 |
| DE | 102010034893 A1 | 2/2012 |

(Continued)

OTHER PUBLICATIONS

Office Action from the corresponding European Patent Application No. 15191212.8-1654 dated Apr. 20, 2016.

*Primary Examiner* — Jacqueline Woznicki
(74) *Attorney, Agent, or Firm* — Workman Nydegger

(57) ABSTRACT

A foot prosthesis having an upper part and a lower part, which is set on the ground as the user walks, one part being arranged on top of the other a certain distance away. The two parts are connected to each other at the tip of the foot. The upper part and the lower part are formed by a one-piece component. In the area near the heel, an elastic damping element is arranged between the upper part and the lower part and is connected to the upper part and/or to the lower part. A compressible but longitudinally strong connecting element, which connects the upper part to the lower part, and which is guided through a recess in the damping element, is provided.

14 Claims, 7 Drawing Sheets

(56) References Cited

U.S. PATENT DOCUMENTS

2014/0012397 A1   1/2014   Mosler et al.

FOREIGN PATENT DOCUMENTS

| DE | 102011014994 | 9/2012 |
| DE | 102012006023 A1 | 10/2012 |
| EP | 2420212 | 2/2012 |
| EP | 2644167 | 10/2013 |
| WO | WO2007085228 | 8/2007 |

* cited by examiner

FOOT PROSTHESIS

CROSS-REFERENCE TO RELATED APPLICATIONS

The present application claims priority of DE 10 2014 117 210.8, filed Nov. 25, 2014, the priority of this application is hereby claimed and this application is incorporated herein by reference.

BACKGROUND OF THE INVENTION

The invention pertains to a foot prosthesis.

Many different types of foot prostheses are known. The goal of each foot prosthesis is to make the foot-fall as comfortable as possible, to cushion it on the basis of the elastic properties of the prosthesis, and to make it possible for the user to walk in a manner close to that in which one would walk with a real foot. One of the known foot prostheses comprises a lower part, which is set down on the ground when walking. Arranged on the lower part is an elastic damping element, which is arranged with an offset primarily toward the heel area. On this elongated damping element, a metal plate with a suitable fastening element such as a pyramid receiver is provided, on which a connecting shaft or the like, by which the entire prosthesis is attached to the leg stump, can be arranged. The damping element gives the plate a certain elastic mobility relative to the lower part. To achieve a certain pretension within the damping element, cable or strap loops are provided in front of and behind the connecting means, for example, the pyramid receiver, on the plate side; these loops pass over the plate, proceed to the lower part, and are either fastened to the lower part or pass under it. By this means the retaining plate is permanently connected to the lower part, i.e. put under tension with respect to it. These cable or strap connections are flexible to the extent that the retaining plate can move elastically toward the lower part, this being true both in the rear heel area and in the forward area located more-or-less in the middle of the foot. Nevertheless, the outward elastic movement and thus the relaxation of the damping element is limited by the cable or strap loops, so that the pretension remains in effect. This doubly limited movement ultimately results in a limitation of the mobility of the lower part relative to the plate. When the heel section is set down, inward deflection at the heel is possible, but the forward end, where the retaining plate is located, cannot follow, because its movement is limited by the cable or strap loop present there. As the foot rolls off at the tip, the retaining plate can deflect inward in the forward area relative to the lower part, but an outward deflection in the heel area is not possible, because the relative mobility is limited by the cable or strap connection present there. This means that there is only a limited ability to move around the actual center of rotation between the rear foot and the forefoot lever, i.e., between the retaining plate and the lower part, because the movement is limited in both directions.

SUMMARY OF THE INVENTION

The invention is thus based on the problem of providing a foot prosthesis which is improved in comparison to the prior art.

To solve this problem, the invention proposes a foot prosthesis comprising an upper part and a lower part, which is set down on the ground when walking, the one part being arranged above the other, the two parts being a certain distance apart but joined to each other at the tip of the foot, wherein the upper part and the lower part are formed by a one-piece component, and wherein, in the area near the heel, an elastic damping element is arranged between the upper part and the lower part and is connected to the upper part and/or to the lower part, wherein a compressible but longitudinally strong connecting means is provided, which is guided through a recess in the damping element.

According to the invention, the foot prosthesis provides, first, a one-piece component forming the upper part and the lower part, preferably made of a carbon fiber composite material; it is therefore preferably a multi-layer laminated component. The upper and lower parts are connected to each other by a foldover in the foot tip area, wherein the foldover proceeds around an angle of, for example, 135-180°. The connecting means, i.e., the pyramid receiver, for example, is located on the upper part. The upper and lower parts are a certain distance apart but are approximately congruent to each other. Between them, in the heel area, the elastic damping element, made of for example, a rubber-like material, is arranged, which, as described above, serves to cushion the foot-fall, and which therefore damps the relative movement of the upper part relative to the lower part. The two parts are therefore coupled to each other by the damping element; in the area between the damping element and the tip of the foot, they form a spring, which, as the user walks, is bent and thus put under load. The damping element is usually bonded two-dimensionally to the upper and/or the lower part; it is usually bonded by means of an adhesive.

According to the invention, a compressible but longitudinally strong connecting means is provided, which connects the upper and lower parts together, wherein this connecting means is guided directly in a recess in the damping element. This means ultimately that the damping means is guided by the center of rotation, formed by the damping element. Because the damping means is in the area near the heel, in which ultimately the pyramid receiver is also arranged, the connection of the upper part to the lower part is therefore also provided in the area underneath the pyramid receiver. This connecting means is compressible; that is, it gives way under load, so that the damping element can deflect inward. It also has considerable tensile strength, however, which means that the outward deflection of the damping element is limited by the connecting means. The connecting means, when in the unloaded state, defines the maximum distance between the upper part and the lower part in this area.

Because, according to the invention, the connecting means is guided by the damping element and thus by, so to speak, the center of rotation, the movement of the upper part relative to the lower part and thus the pivoting around the center of rotation is limited by this connecting means neither in the heel area, nor in the mid-foot area situated in front, nor in the area of the tip of the foot. As a result, the damping element can deflect inwardly and thus the upper part can pivot versus the lower part more-or-less around the center of rotation over a relatively wide range and without limitation, which means that the ability of the upper part to move relative to the lower part is considerably improved. The deflection distance is thus not limited as long as the springs are not in contact, which occurs at the end of the movement as the foot rolls over the tip. When the springs are in contact, i.e., when the upper part makes contact with the lower part, what can be called the "virtual center of rotation" migrates forward from the damping element to the contact point of the upper part with the lower part, and this connection tensions the upper part against the lower part, which leads in turn to a progressive increase in the force. There is therefore a considerable amount of relative mobility between the upper part and the lower part in the longitudinal direction of the foot, which is achieved in particular by the use of a single connecting means to couple the two parts, which connecting means passes through the damping element. In addition, there is also a contribution to be expected from the fact that the damping element is preferably not connected to the upper part, so that, in the extreme case, the upper part is able to move in the longitudinal direction of the foot relative to the damping element. It is prevented from being lifted off by the longitudinally strong connecting means.

Overall, the foot prosthesis according to the invention therefore makes it possible for the user to walk much more comfortably and in a manner closer to that possible with a real foot. The shear forces which occur in the anterior-posterior direction are not completely suppressed, because no cable and strap connections, as described above, are provided to limit the movement, as a result of which there are no abrupt interruptions in the rolling movement which can be perceived by the user.

The connecting means itself is preferably a cable or a strap, wherein the cable or strap can be made of high-strength, abrasion-resistant plastic fibers or of steel wire.

With respect to the embodiment of the connecting means and its attachment, various alternatives are conceivable. According to a first alternative of the invention, the cable or strap forms a loop, wherein the ends are attached to a common retaining element, which is fastened to the lower part, whereas the loop is attached to the upper part by a loop-retaining element, which passes through the loop. In this configuration, the connecting means is connected only to the lower part, to which the retaining element is appropriately attached, whereas the loop is held in place on the upper part by an appropriate loop-retaining element.

This loop-retaining element is preferably a pin, which rests on the top surface of the upper part and which passes through the loop, the loop itself passing through an opening in the upper part. The pin therefore serves as an anchor, around which the loop is wrapped. The pin is supported on the top surface of the upper part, so that a permanent connection of the upper part to the lower part is thus established.

It is advisable for a retaining element to be arranged on the upper part to prevent the pin from shifting axially. By means of this retaining element, which is arranged on the top surface of the upper part, the pin is therefore held in its position; it therefore cannot move in its longitudinal direction or, in the extreme case, slip out of the loop. The retaining element is, for example, configured as a plate and can comprise one or two projecting tabs, which engage in the opening in the upper part, and two additional tabs, between which the pin is held. As a result of the plate-like configuration, the retaining element does not have excessive height. By means of the one or two tabs projecting from the lower surface of the plate and engaging in the opening in the top surface, through which the loop passes, the retaining element is held in its position in the transverse reaction, i.e., in the longitudinal direction of the pin attached to it, and therefore cannot itself move in this direction. The pin itself is held in place between two additional tabs, which project from the top surface of the retaining element.

A retaining element configured in this way is especially easy to manufacture in the form of a sheet-metal retaining plate. The corresponding opening in the retaining element, through which the loop passes, and the tabs can be easily formed by a simple stamping operation.

Alternatively, the pin can also be inserted into a retaining plate arranged on the top surface of the upper part. Provided that the upper part is configured appropriately, the retaining plate can, for example, carry the fastening means, i.e., the pyramid receiver, for example. Because, in a prosthesis configuration of this type, the retaining plate is to be arranged above the damping element, it is a logical in this case for the pin to be held in the retaining plate.

The opening through which the loop passes is preferably configured as a slot, which extends along the upper part. This slot can extend, for example, up to the middle area of the prosthesis; it therefore has a certain length. It even makes possible, in the extreme case, a certain mobility of the loop, i.e., of the pin, in the slot, insofar as the pin rests directly on the surface. As previously described, during the course of the rolling movement, the upper part and the lower part come in contact, and as the rolling continues, the force increases significantly, this being associated with a relative displacement of the upper part relative to the lower part. The loop and the pin can ultimately follow this displacement if necessary, because, as a result of the configuration of the slot, they are able to move slightly. As an alternative to the configuration of the slot, it is also possible, obviously, to provide the opening in the form of a simple hole.

According to an embodiment of the invention representing an alternative to the one just described in which the cable or strap is held in place by a pin, each of the two ends of the cable or strap is attached to its own retaining element, wherein the one retaining element is attached to the lower part, the other retaining element to the upper part. Here, therefore, the cable or strap runs in a straight line from the lower part of the upper part and is fastened appropriately to the retaining elements there.

A retaining element of this type, independently of whether or not one or two are provided, is preferably configured as a sleeve, in which the cable or strap is adhesively bonded, cast, or clamped, wherein the sleeve passes through an opening in the lower part or upper part. For example, a radial collar is provided on the sleeve; the collar rests on the lower part or, if a similar sleeve is to be fastened to the upper part, on the upper part, too. Both in the loop embodiment and in the embodiment without a loop, the cable or strap is first adhesively bonded, cast, or clamped in the sleeve to be fastened to the lower part, wherein preferably the casting or adhesive bonding technique is used. Then the sleeve is set in the lower part, and the cable or strap is guided through the opening in the damping element. The sleeve is now fastened to the lower part, also by adhesive bonding or casting, for example. Then the upper part is pressed firmly against the lower part, so that the damping element is compressed. This makes it possible to push the pin through the loop passing through the slot and to position it appropriately on the upper part or on the retaining plate, whereupon the pressure is released. Thus the connecting means is fully assembled. If a second sleeve is required on the upper part, the end of the cable present there is inserted into the sleeve, adhesively bonded or cast in place, after which, upon completion of the curing of the casting compound or of the adhesive, the pressure is released, and the sleeve is fastened in a corresponding fashion to the upper part by means of a corresponding radial collar, for example. The sleeve can, of course, extend a certain distance into the elastomer, which appropriately comprises an area of thicker material here.

According to a third embodiment of the connection between the cable or strap to the upper part and to the lower part, the cable or strap is laminated directly into the upper part and the lower part. As described, the component forming the lower part or upper part consists preferably of a carbon fiber composite material, which usually consists of several carbon fiber layers laminated on top of each other. As part of this production process, it is now conceivable that the fibers or wires of the cable or strap can be laminated at the same time into the upper part and lower part, so that ultimately what is obtained is a one-piece component. The only remaining step required is to mount the damping element, which, for this purpose, should, of course, have a slot-like opening, and to push it between the upper part and the lower part.

As described above, it is essential for the cable or strap to pass through an appropriate recess in the damping element. This recess can be executed as a through-hole or as a slot, which, if desired, can be open on one side of the damping element. If the damping element has already been bonded to the lower part before the cable or strap is installed, the recess is preferably executed as an opening, through which the cable or strap can be guided. If the cable or strap has been installed previously, then the recess is advisably executed as a slot, so that, as the damping element is pushed between the upper part and the lower part, the cable or strap will slide into the slot.

To vary the damping behavior, at least one stiffening element, which influences the damping behavior, can be attached to the damping element. For this purpose, a plug-in receptacle, for example, can be provided in the damping element, into which the stiffening element can be plugged. This can be a positive connection; that is, the plug-in receptacle and the stiffening element both have a geometric form. A stiffening element of this type, made of a plastic with a hardness different from that of the damping element, for example, can now be provided on the rear side of the heel of the damping element, or possibly also on the opposite side.

Finally, a cover, arranged detachably on the upper part, can be provided to cover the fastening area of the connecting means, wherein a cover of this type is necessary, of course, only when the cable or strap is held in place either by the pin or by a sleeve mounted on the upper surface.

The various features of novelty which characterize the invention are pointed out with particularity in the claims annexed to and forming a part of the disclosure. For a better understanding of the invention, its operating advantages, specific objects attained by its use, reference should be had to the drawings and descriptive matter in which there are illustrated and described preferred embodiments of the invention.

DETAILED DESCRIPTION OF THE INVENTION

Figure 1:
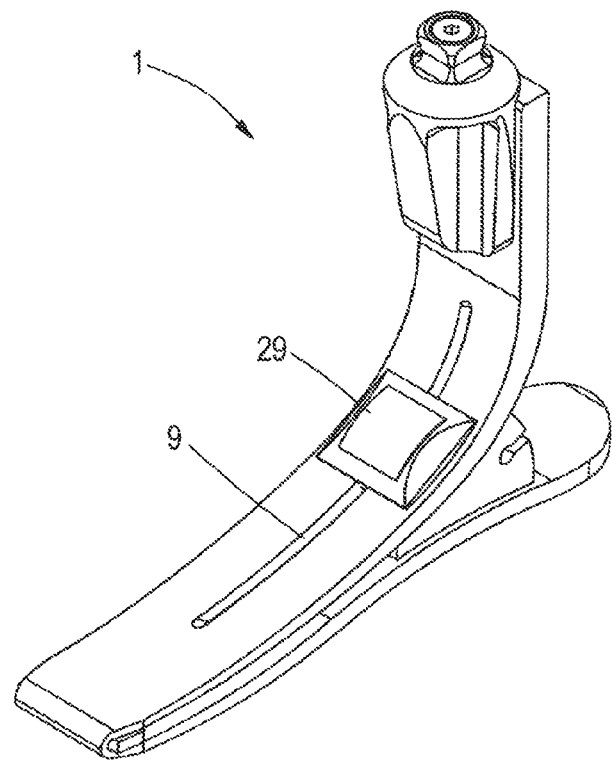
FIG. 1 shows a perspective view of a foot prosthesis according to the invention.
Figure 2:
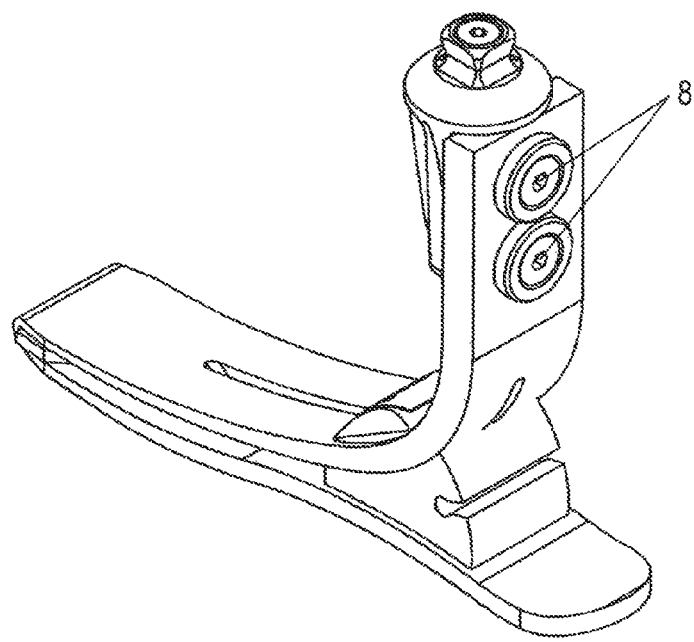
FIG. 2 shows a perspective view rotated by 90°.
Figure 3:
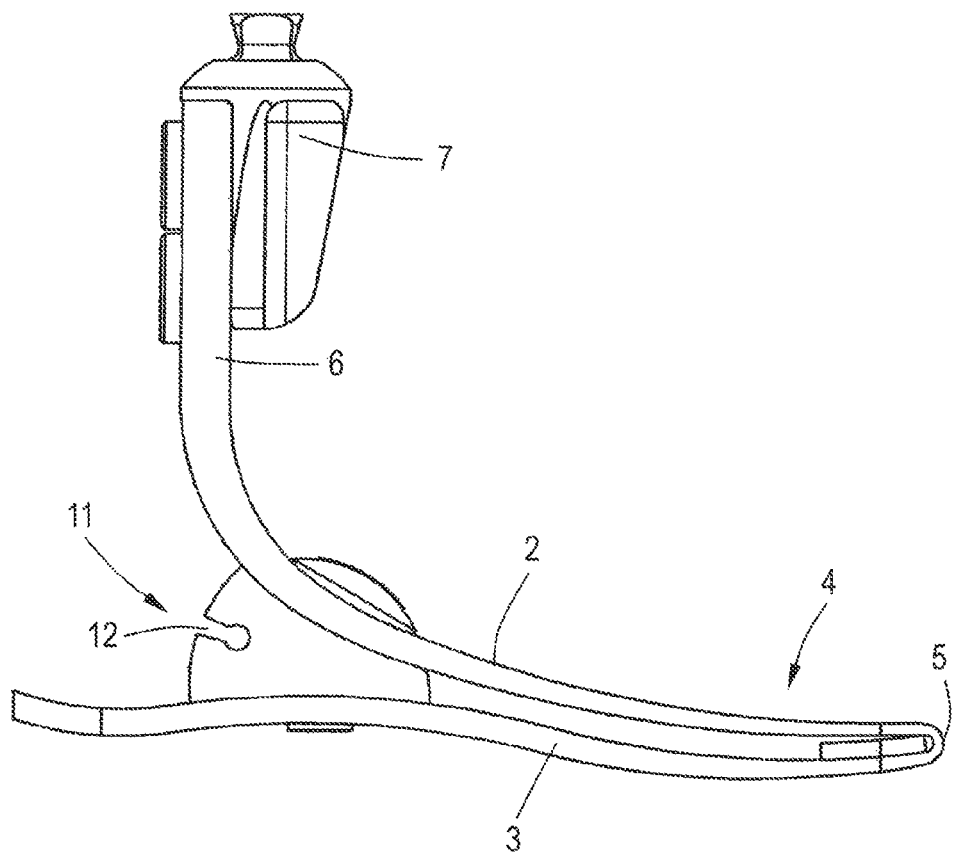
FIG. 3 shows a side view of the foot prosthesis.
Figure 4:
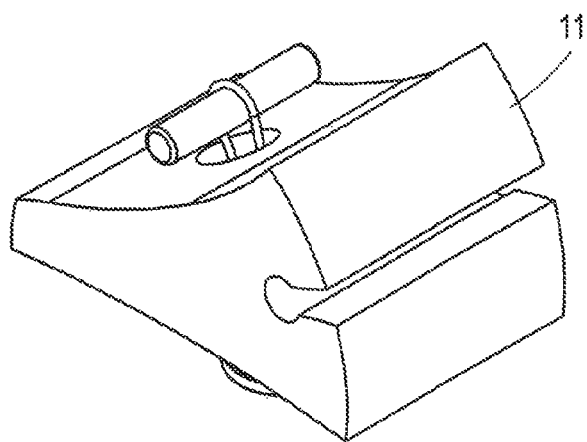
FIG. 4 shows a perspective view of the damping element with its associated connecting means at an angle from above.
Figure 5:
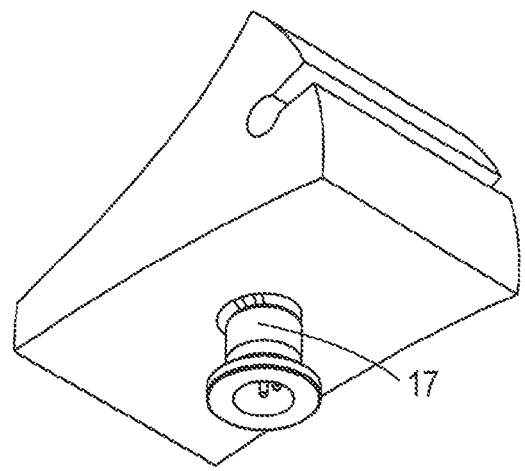
FIG. 5 shows the arrangement of FIG. 4 at an angle from below.
Figure 6:
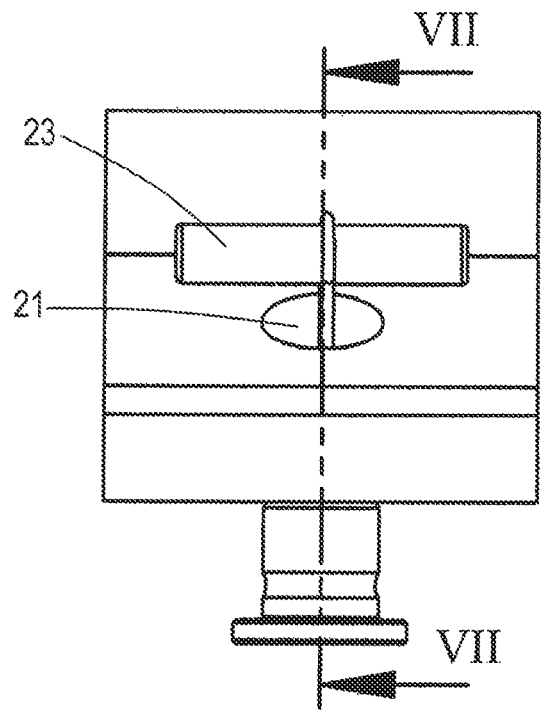
FIG. 6 shows a front view of the arrangement of FIG. 4.

FIG. 1 shows a foot prosthesis 1 according to the invention, consisting of an upper part 2 and a lower part 3; see also FIGS. 2 and 3. The upper part 2 and the lower part 3 are realized by a one-piece component 4, wherein the upper part 2 and the lower part 3 are connected to each other in the area of the tip of the foot by a foldover 5. In this exemplary embodiment, the upper part 2 ends in a vertical section 6, on which a fastening means 7 is arranged for the connection of, for example, a prosthesis shaft by means of suitable mounting screws 8.

The component 4 is a one-piece component, preferably made of a carbon fiber composite material. This means that the upper part 2 and the lower part 3 can be formed in a single production step. As can be seen, the upper part 2 and the lower part 3, when seen from above, are congruent with each other, i.e., their outlines coincide.

Figure 7:
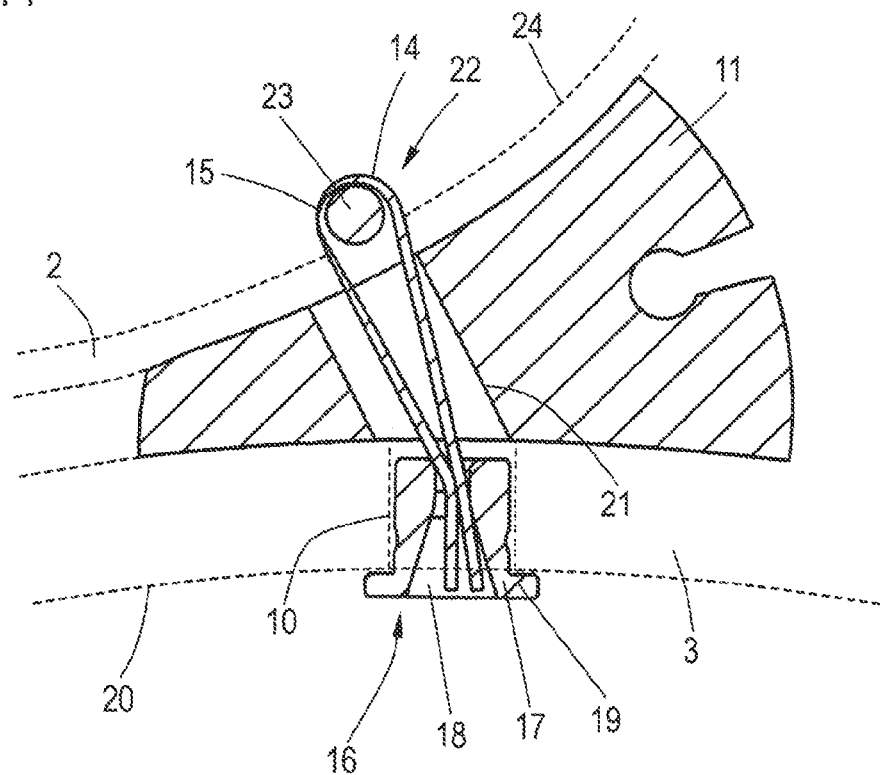
FIG. 7 shows a cross-sectional view through the arrangement in the direction of line VII-VII in FIG. 6.

An elongated slot 9 is provided in the upper part 2; this slot will be discussed again below. An opening 10 is formed in the lower part 3 (see FIG. 7); this will also be discussed again below. Slot 9 and opening 10 make it possible to accommodate a connecting element—again, to be discussed below.

Between the upper part 2 and the lower part 3, a damping element 11 of an elastic, rubber-like material is arranged. It is preferably permanently connected only to the lower part 3 by means of, for example, an adhesive. On the rear side of the damping element 11, near the heel, a plug-in receptacle 12 is formed, into which, as needed, a plug element (not shown in detail here) can be inserted to vary the damping behavior; the plug is held positively in place in the receptacle. A cover 29 is arranged detachably on top of the upper part 2.

FIGS. 4-7 show in detail the damping element 11 and the connecting means 13 passing through it, by means of which the upper part 2 and the lower part 3 are connected to each other. The damping element comprises an opening 21, which, in the example shown here, is executed as a simple through-hole—see especially the cross-sectional view in FIG. 7. The connecting means 13 in this exemplary embodiment comprises a cable 14, preferably a cable made of plastic fibers, although the use of wire cable is also conceivable. The cable 14 is configured as a loop 15. Both ends of the cable 14 are held in a retaining element 16, here in the form of a sleeve 17, and are permanently anchored therein by means of a casting compound 18. In the assembled state, the sleeve 17 is inserted into the opening 10 in the lower part and rests by a radial collar 19 on the bottom surface 20 of the lower part 3.

The cable 14 is guided through the opening 21 in the damping element 11 and emerges toward the upper part 2. It passes through the upper part 2 at the slot 9, i.e., it is therefore guided through the slot 9. A loop-retaining element 22, here in the form of a pin 23, is inserted through the loop 15. In the assembled position, the pin 23 (see the cross-sectional view in FIG. 7) lies on the top surface 24 of the upper part 2. This is how the cable 14 is attached to the upper part 2.

The connecting means 13, therefore, realizes a compressible but longitudinally strong connection of the upper part to the lower part, wherein the connecting means 13 extends through the damping element 11. Because, as the user walks, the damping element 11 ultimately forms the center of rotation, around which the upper part rotates relative to the lower part between the time that the heel is set down and the time that the roll-off across the tip of the foot occurs, there is therefore no limitation of any kind on the movement, i.e., on the lever action in the rear-foot and front-foot lever area.

Figure 8:
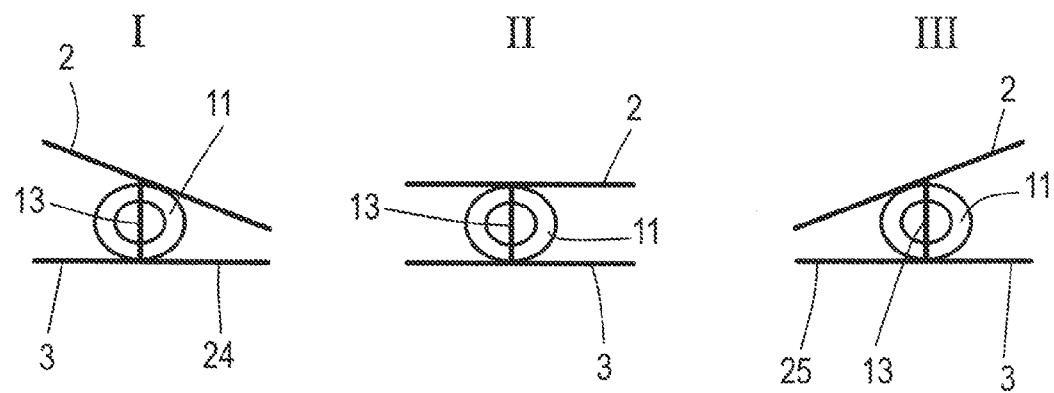
FIG. 8 shows a schematic diagram of three different walking situations to explain the mobility of the upper part relative to the lower part.

The schematic diagrams according to FIG. 8 make this clear. FIG. 8, in the form of three schematic diagrams I, II, and III, shows the relative movement of the upper part 2 versus the lower part 3. Let it be assumed that view I shows the heel set-down process, i.e., the time at which the heel section 24 of the lower part 3 is set down onto the ground. As can be seen, the upper part 2 pivots or deflects inward toward the heel, without the connecting means 13, that is, the cable connection, limiting this movement in any way. FIG. 8 shows the pivoting areas in question in exaggerated form, so that the basic principle can be readily understood.

Diagram II shows the state which is present when the lower part of the prosthesis is resting flat on the ground. The upper part 2 is located directly above the lower part 3, under only vertical load, wherein the connecting means 13 interferes in no way whatever with the transition from the situation according to Diagram I to that of Diagram II.

Diagram III, finally, shows the roll-off process across the tip 25 of the lower part 3. Here the upper part 2 can deflect inward in the area of the tip toward the lower part 3, whereas, in the heel area, a spreading-apart movement is possible. This movement not impeded or restricted in any way by the connecting means 13.

The prosthesis according to the invention thus guarantees that the shear forces occurring in the anterior-posterior direction are not completely suppressed, i.e., the connecting means offers no interference whatever to the relative mobility, as a result of which no abrupt interruptions which could be felt by the user during the course of the roll-off movement are produced. On the contrary, the set-down and roll-off processes are rounded and homogeneous.

Figure 9:
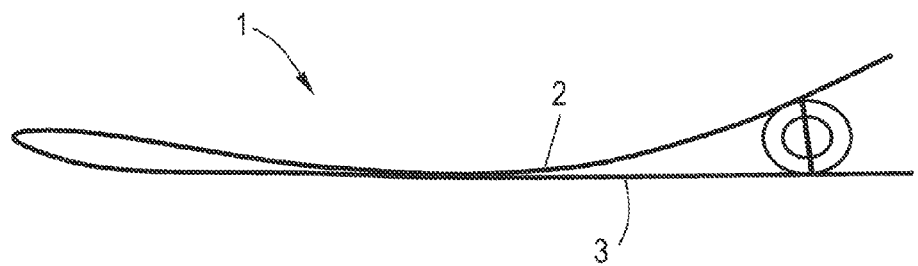
FIG. 9 shows another associated schematic diagram.

FIG. 9 shows a schematic diagram of the entire foot prosthesis 1, corresponding to the schematic diagrams of FIG. 8. As can be seen, as the user walks, the upper part 2 comes to rest on the lower part 3 during the transition from Diagram II to Diagram III. During this contact, the virtual center of rotation migrates from the damping element 11 to the contact point between the upper part 2 and the lower part 3. The spring formed by the upper part 2 and the lower part 3 is therefore put under opposing tension, and thus the force increases progressively as the roll-off movement continues.

Figure 10:
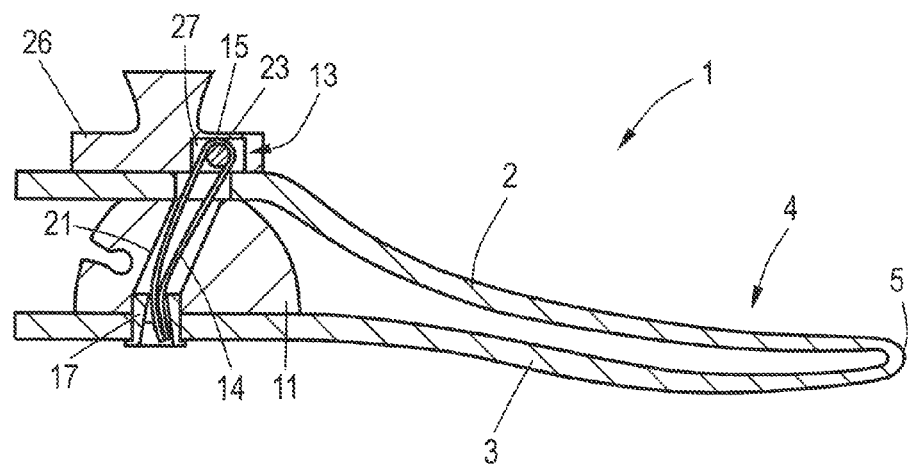
FIG. 10 shows a cross-sectional view through a foot prosthesis of a second embodiment.

FIG. 10 shows another embodiment of a foot prosthesis 1 according to the invention, wherein the same reference numbers are used for the same components. Here, too, there is an upper part 2 and a lower part 3, which consist of a one-piece carbon fiber composite component 4. They are again connected to each other by a foldover 5.

A damping element 11 is again provided between the upper part 2 and the lower part 3, wherein, in this embodiment, the upper part 2 has a different geometry than that of the embodiment previously described. Here the upper part 2 is more-or-less parallel to the lower part 3 as it proceeds toward the heel area. A retaining plate 26 is arranged on the upper part 2; this plate carries the fastening element, to which the connecting shaft, for example, is attached.

A connecting means 13, comprising a cable 14, which forms a loop 15, is provided here also. The lower ends of the cable are again held in a sleeve 17, which is fastened to the lower part in a manner similar to that described in conjunction with the preceding figures.

The cable 14 again passes through an opening 21 in the damping element 11. It is guided through an opening provided in the upper part 2 to a recess 27 in the retaining plate 26, in which recess a pin 23 is inserted, around which, again the loop 15 is wrapped. The pin 23 is thus held in place in an appropriately configured receptacle in the retaining plate 26. In this case, therefore, the pin 23 is not attached directly to the upper part 2 but rather to the retaining plate 26 fastened to the top surface.

Figure 11:
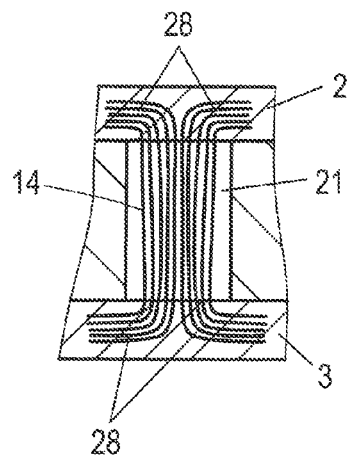
FIG. 11 shows a schematic diagram of another possibility of attaching the cable or strap.

FIG. 11 shows another embodiment, in which the cable 14 is laminated directly into the upper part 2 and the lower part 3. In the schematic diagram, the individual cable fibers 28 are shown, which are incorporated directly into the laminate or resin matrix of the upper part 2 and lower part 3. They pass through the damping element 11, which, in this embodiment, is put into place only afterwards; for this purpose, the damping element 11 comprises, for example, a suitable slot, which leads to the corresponding opening 21, so that, as the damping element 11 is being pushed between the upper part 2 and the lower part 3, the cable 14 will slide through the slot and into the opening.

Figure 12:
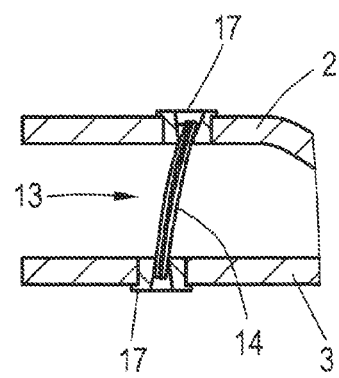
FIG. 12 shows a schematic diagram of another possibility of attaching the cable or strap with two sleeves.

FIG. 12, finally, shows an embodiment in which the connecting means 13 comprises a sleeve 17 attached to the lower part 3 and also a sleeve 17 attached to the upper part 2. Each of the two ends of the cable 14 is thus fixed in place in one of the two sleeves 17; a loop is not formed in this embodiment. The function, however, is in principle the same as that described above in conjunction with the preceding embodiments.

Figure 13:
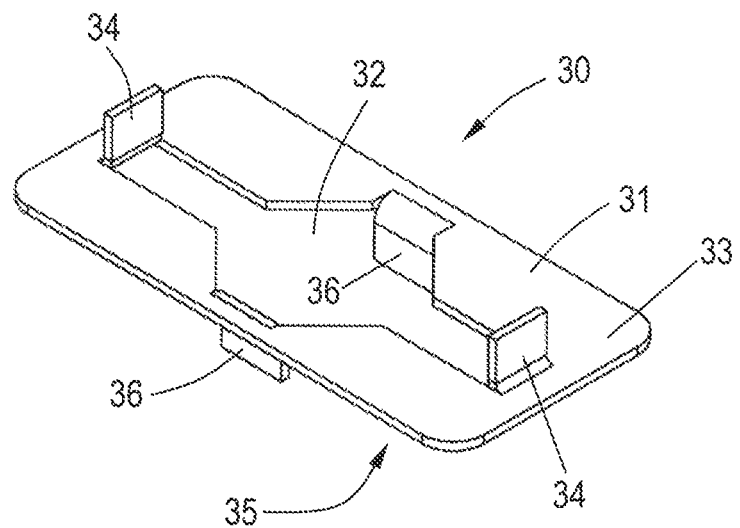
FIG. 13 shows a perspective view of a retaining element in the form of a sheet-metal plate.
Figure 14:
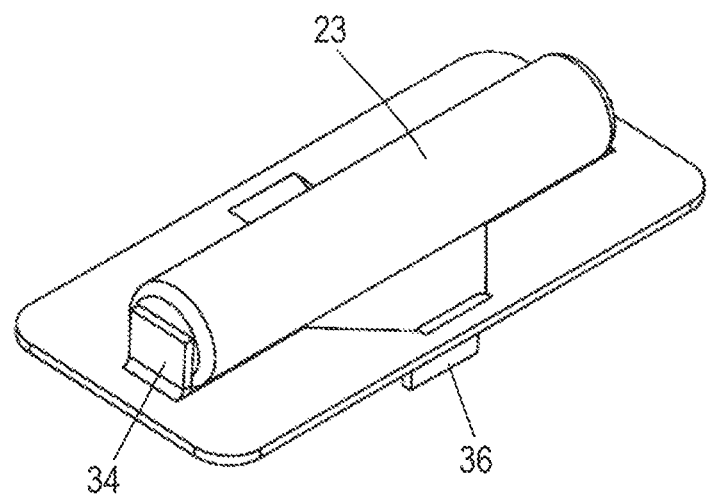
FIG. 14 shows a perspective view of the retaining element with a pin arranged on it.

FIG. 13 shows a retaining element 30 in the form of a flat retaining plate 31, which serves to hold the pin provided in the embodiments according to FIGS. 1-7. The retaining plate 31 comprises a central opening 32. On the top surface 33, two tabs 34, projecting from the top, are provided, between which (see FIG. 14), the pin 23 is accommodated. As a result, the pin is held axially; it cannot move in its longitudinal direction.

On the bottom 35 of the retaining plate 31, two additional tabs 36 are provided, which are positioned centrally between the tabs 34, but, as indicated above, project toward the other side. The tabs 36 engage in the slot 9 (see the diagram according to FIG. 15). As a result of this engagement of the tabs, the retaining plate 31 itself is secured against lateral displacement, so that it cannot move in this direction.

Figure 15:
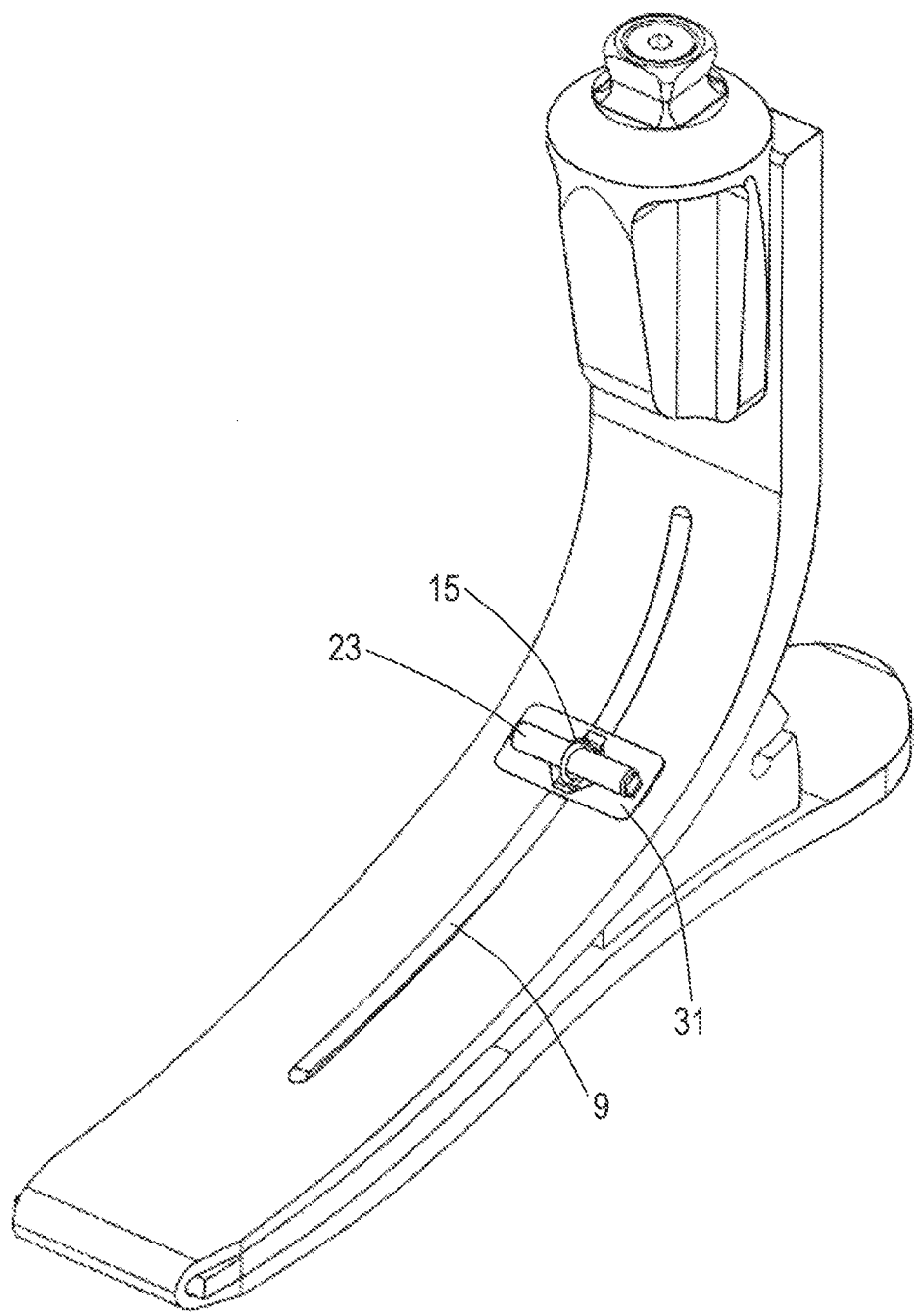
FIG. 15 shows a perspective view of a foot prosthesis according to the invention with a retaining element and a pin.

In the assembled state shown in FIG. 15, the loop 15 passes through the slot 9 and through the opening 32 in the retaining plate 31; the pin 23 for its own part passes through the loop 15. The pin itself is accommodated in the elongated opening 32, which, as shown in FIG. 13, extends from one tab 34 to the other table 34; the pin therefore cannot move in this direction either, i.e., it cannot slip away from the retaining plate 21. This means that, even in the case of a slight movement along the slot 9, the retaining plate 31 and the pin 23 will always move jointly. The pin 23 cannot become separated from the retaining plate 31 or from the loop 15.

While specific embodiments of the invention have been shown and described in detail to illustrate the inventive principles, it will be understood that the invention may be embodied otherwise without departing from such principles.

We claim:

1. A foot prosthesis, comprising:
   a lower part and an upper part defining a top surface and connected to the lower part in a toe area of the foot prosthetic;
   an elastic damping element positioned between the upper part and the lower part in a heel area of the foot prosthetic, the elastic damping element connected to the lower part; and
   a cable connecting the upper part to the lower part, the cable being guided through a recess in the damping element; and
   a retaining element secured to the cable and engageable with the top surface of the upper part, the retaining element arranged to move along a length of the top surface of the upper part when the upper part is displaced relative to the lower part.

2. The foot prosthesis of claim 1, wherein the retaining element comprises a pin.

3. A foot prosthesis, comprising:
   a lower part and an upper part defining a top surface and connected to the lower part in a toe area of the foot prosthetic
   an elastic damping element arranged between the upper part and the lower part in a heel area of the foot prosthetic, the elastic damping element connected to at least one of the upper part and/or to the lower part;
   a connecting part comprising a cable or strap having a compressible but longitudinally strong configuration, the connecting part connecting the upper part and the lower part, and which is and being guided through a through-hole or slot in the damping element; and
   a retaining element secured to the connecting part and engageable with the top surface of the upper part, the retaining element arranged to move along a length of the top surface of the upper part when the upper part is displaced relative to the lower part.

4. A foot prosthesis, comprising:
   a lower part and an upper part defining a top surface and connected to the lower part in a toe area of the foot prosthetic
   an elastic damping element arranged between the upper part and the lower part in a heel area of the foot prosthetic, the elastic damping element connected to at least one of the upper part and/or to the lower part; and
   a connecting part comprising a cable or strap having a compressible but longitudinally strong configuration, the connecting part connecting the upper part and the lower part, and which is and being guided through a recess in the damping element; and
   a retaining element secured to the connecting part and engageable with the top surface of the upper part, the retaining element arranged to move along a length of the top surface of the upper part when the upper part is displaced relative to the lower part.

5. The foot prosthesis according to claim 4, wherein the connecting part is made of plastic fibers or of steel wire.

6. The foot prosthesis according to claim 4, wherein the cable or strap forms a loop held in place in by a lower retaining element.

7. The foot prosthesis according to claim 6, wherein the retaining element is a pin that passes through the loop, the loop extending through an opening in the upper part.

8. The foot prosthesis according to claim 7, wherein the opening is executed as a slot, which extends along the upper part, or as a hole.

9. The foot prosthesis according to claim 4, wherein a sleeve is adhesively bonded to the connecting part.

10. The foot prosthesis according to claim 4, wherein the recess provided in the damping element is a through-hole or slot.

11. The foot prosthesis according to claim 4, wherein at least one stiffening element is attached to the damping element, the stiffening element arranged to influence a damping effect of the damping element.

12. The foot prosthesis according to claim 11, wherein a plug-in receptacle is provided in the damping element.

13. The foot prosthesis according to claim 4, wherein a cover is detachably arranged on the upper part, the cover covering the connecting part along the top surface of the upper part.

14. The foot prosthesis according to claim 4, wherein the upper part and the lower part comprise a carbon fiber composite material.

\* \* \* \* \*